United States Patent [19]

Weichert et al.

[11] Patent Number: 5,747,541
[45] Date of Patent: May 5, 1998

[54] SUBSTITUTED BENZOYLGUANIDINES, A PROCESS FOR THEIR PREPARATION, THEIR USE AS MEDICAMENT OF DIAGNOSTIC AGENT, AND MEDICAMENT COMPRISING THEM

[75] Inventors: Andreas Weichert, Egelsbach; Joachim Brendel, Vilbel; Heinz-Werner Kleemann, Bischofsheim; Hans Jochen Lang, Hofheim; Jan-Robert Schwark, Frankfurt; Udo Albus, Florstadt; Wolfgang Scholz, Eschborn, all of Germany

[73] Assignee: Hoechst Aktiengesellschaft, Frankfurt am Main, Germany

[21] Appl. No.: 873,825

[22] Filed: Jun. 12, 1997

Related U.S. Application Data

[63] Continuation of Ser. No. 715,685, Sep. 18, 1996, abandoned.

[30] Foreign Application Priority Data

Sep. 27, 1995 [EP] European Pat. Off. .............. 95115240

[51] Int. Cl.$^6$ ...................... A61K 31/165; C07C 231/02; C07C 235/50
[52] U.S. Cl. .................. 514/622; 514/618; 514/619; 514/621; 564/133; 564/134; 564/139; 564/142; 564/162; 564/164; 564/167; 564/176; 564/177
[58] Field of Search ............................ 514/618, 619, 514/621, 622; 564/133, 134, 139, 142, 162, 164, 167, 176, 177

[56] References Cited

U.S. PATENT DOCUMENTS

| | | | |
|---|---|---|---|
| 3,780,027 | 12/1973 | Cragoe et al. | 260/239.6 |
| 5,091,394 | 2/1992 | Englert et al. | 514/331 |
| 5,292,755 | 3/1994 | Englert et al. | 514/331 |
| 5,364,868 | 11/1994 | Englert et al. | 514/331 |
| 5,373,024 | 12/1994 | Lang et al. | 514/618 |
| 5,516,805 | 5/1996 | Lang et al. | 514/620 |
| 5,547,953 | 8/1996 | Weichert et al. | 514/226.5 |
| 5,567,734 | 10/1996 | Schwark et al. | 514/617 |

FOREIGN PATENT DOCUMENTS

| | | |
|---|---|---|
| 3301393 | 8/1993 | Australia . |
| 3301493 | 8/1993 | Australia . |
| 3301593 | 8/1993 | Australia . |
| 4163594 | 1/1994 | Australia . |
| 4746093 | 3/1994 | Australia . |
| 5236893 | 6/1994 | Australia . |
| 5249093 | 6/1994 | Australia . |
| 5271693 | 7/1994 | Australia . |
| 5522994 | 8/1994 | Australia . |
| 6454394 | 12/1994 | Australia . |
| 6454494 | 12/1994 | Australia . |
| 4221896 | 2/1995 | Australia . |
| 6881194 | 2/1995 | Australia . |
| 7022294 | 2/1995 | Australia . |
| 7250794 | 3/1995 | Australia . |
| 1135395 | 8/1995 | Australia . |
| 1799995 | 11/1995 | Australia . |
| 2172095 | 1/1996 | Australia . |
| 2330095 | 1/1996 | Australia . |
| 3050495 | 3/1996 | Australia . |
| 3050596 | 3/1996 | Australia . |
| 3050695 | 3/1996 | Australia . |
| 3900895 | 5/1996 | Australia . |
| 0556674 | 8/1993 | European Pat. Off. . |
| 0602522 | 6/1994 | European Pat. Off. . |
| 9426709 | 11/1994 | WIPO . |

OTHER PUBLICATIONS

Duff et al., Circulation, 79(6), 1257–63 (1989).
Schmid et al., Biochemical and Biophysical Research Comm. 112–117 (1992).
Scholz et al., Cardiovascular Res. 29(2): 260–268 (1995).
Rosskopf, et al., Cellular Physiology Biochem (5)4, 269–275 (1995).
Scholz, et al., Basic Research Cardiology 88(5), 443–55 (1993).
Sack, et al., J. Cardiovasc. Pharmacol. 23(1), 72–78 (1994).
Kranzhofer, et al., Circ. Res. 73(2); 264–8 (1993).
Scholz, et al., Br. J. Pharmacol 109(2); 562–8 (1993).
Scholz, et al., J. Mol. Cell. Cardiol. 24(7), 731–39 (1992).
Scholz et al., Cardiovascular Research vo. 29(2), 184–188 (1995).
Hoppe–Seyler, Biological Chemistry vol. 372 No. 9, p. 750 (1991).
Faber et al., Cell. Physiol Biochem 61(1–2), 39–49 (1996).
Busch et al., Pfluegers Arch. 431(5), 690–96 (1996).
Englert, et al., Eur. J. Pharmacol 210(1), 69–75 (1992).
Mitsuka et al, Circulation Research vol. 73(2): 269–275 (1993).
M. Nassal, Liebigs Ann. Chem.:1510–1523 (1983).

*Primary Examiner*—Peter O'Sullivan
*Attorney, Agent, or Firm*—Finnegan, Henderson, Farabow, Garrett & Dunner, L.L.P.

[57] ABSTRACT

The present invention relates to substituted benzoylguanidines, a process for their preparation, their use as medicament or diagnostic agent, and medicament comprising them.

21 Claims, No Drawings

SUBSTITUTED BENZOYLGUANIDINES, A PROCESS FOR THEIR PREPARATION, THEIR USE AS MEDICAMENT OF DIAGNOSTIC AGENT, AND MEDICAMENT COMPRISING THEM

CROSS-REFERENCE TO RELATED APPLICATION

This is a continuation of application Ser. No. 08/715,685, filed Sep. 18, 1996, which is herein incorporated by reference, abandoned.

SUMMARY OF THE INVENTION

The invention relates to benzoylguanidines of the formula I

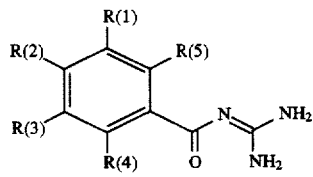

in which:
at least one of the substituents R(1), R(2) and R(3) is

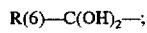

R(6)—C(OH)$_2$—;

R(6) is perfluoroalkyl having 1, 2 or 3 carbon atoms, which is straight-chain or branched;

and the other substituents R(1), R(2) and R(3) are, independently of one another, hydrogen, OH, F, Cl, Br, I, alkyl having 1, 2, 3, 4, 5 or 6 carbon atoms, cycloalkyl having 3, 4, 5 or 6 carbon atoms, alkoxy having 1, 2, 3 or 4 carbon atoms or phenoxy, which is unsubstituted or is substituted by 1–3 substituents chosen from the group consisting of F, Cl, methyl and methoxy;

or the other substituents R(1), R(2) and R(3) are, independently of one another, alkyl-SO$_x$, —CR(7)═CR(8)R(9) or —C°CR(9);

x is zero, 1 or 2;

R(7) is hydrogen or methyl;

R(8) and R(9) are, independently of one another, hydrogen, alkyl having 1, 2, 3 or 4 carbon atoms, cycloalkyl having 3, 4, 5, 6, 7 or 8 carbon atoms or phenyl, which is unsubstituted or is substituted by 1–3 substituents chosen from the group consisting of F, Cl, CF$_3$, methyl and methoxy;

or the other substituents R(1), R(2) and R(3) are, independently of one another, phenyl, C$_6$H$_5$—(C$_1$–C$_4$)-alkyl, naphthyl, biphenylyl, quinolinyl, isoquinolinyl or imidazolyl, where quinolinyl, isoquinolinyl or imidazolyl are bonded via C or N and where phenyl, C$_6$H$_5$—(C$_1$–C$_4$)-alkyl, naphthyl, biphenylyl, quinolinyl, isoquinolinyl and imidazolyl are unsubstituted or are substituted by 1–3 substituents chosen from the group consisting of F, Cl, CF$_3$, CH$_3$, methoxy, hydroxyl, amino, methylamino and dimethylamino;

or the other substituents R(1), R(2) and R(3) are, independently of one another, SR(10), —OR(10) or —CR(10)R(11)R(12);

R(10) is —C$_f$H$_{2f}$—(C$_3$–C$_8$)-cycloalky, quinolinyl, isoquinolinyl, pyridinyl, imidazolyl or phenyl, where the aromatic systems quinolinyl, isoquinolinyl, pyridinyl, imidazolyl and phenyl are unsubstituted or are substituted by 1–3 substituents chosen from the group consisting of F, Cl, CF$_3$, CH$_3$, methoxy, hydroxyl, amino, methylamino and dimethylamino;

f is zero, 1 or 2;

R(11) and R(12) are, independently of one another, defined as R(10), hydrogen or alkyl having 1, 2, 3 or 4 carbon atoms; and R(4) and R(5) are, independently of one another, hydrogen, alkyl having 1, 2 or 3 carbon atoms, F, Cl, Br, I, CN, OR(13), NR(14)R(15) or —(CH$_2$)$_n$—(CF$_2$)$_o$—CF$_3$;

R(13), R(14) and R(15) are, independently of one another, hydrogen or alkyl having 1, 2, 3 or 4 carbon atoms;

n is zero or 1;

o is zero, 1 or 2;

and pharmacologically acceptable salts thereof.

Preferred compounds of the formula I are those in which:
at least one of the substituents R(1), R(2) and R(3) is

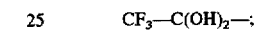

CF$_3$—C(OH)$_2$—;

and the other substituents R(1), R(2) and R(3) are, independently of one another, hydrogen, F, Cl, alkyl having 1, 2, 3, 4, 5 or 6 carbon atoms, cycloalkyl having 3, 4, 5 or 6 carbon atoms, alkoxy having 1, 2, 3 or 4 carbon atoms or phenoxy,
which is unsubstituted or is substituted by 1–3 substituents chosen from the group consisting of F, Cl, methyl and methoxy;

or the other substituents R(1), R(2) and R(3) are, independently of one another, alkyl-SO$_x$, —CR(7)═CR(8)R(9) or —C° CR(9);

x is zero, 1 or 2;

R(7) is hydrogen or methyl;

R(8) and R(9) are, independently of one another, hydrogen, alkyl having 1, 2, 3 or 4 carbon atoms, cycloalkyl having 3, 4, 5, 6, 7 or 8 carbon atoms or phenyl, which is unsubstituted or is substituted by 1–3 substituents chosen from the group consisting of F, Cl, CF$_3$, methyl and methoxy;

or the other substituents R(1), R(2) and R(3) are, independently of one another, phenyl, C$_6$H$_5$—(C$_1$–C$_2$)-alkyl, naphthyl, biphenylyl, quinolinyl, isoquinolinyl or imidazolyl, where quinolinyl, isoquinolinyl or imidazolyl are bonded via C or N and where phenyl, C$_6$H$_5$—(C$_1$–C$_4$)-alkyl, naphthyl, biphenylyl, quinolinyl, isoquinolinyl and imidazolyl are unsubstituted or are substituted by 1–3 substituents chosen from the group consisting of F, Cl, CF$_3$, CH$_3$, methoxy, hydroxyl, amino, methylamino and dimethylamino;

or the other substituents R(1), R(2) and R(3) are, independently of one another, SR(10), —OR(10) or —CR(10)R(11)R(12);

R(10) is —C$_f$H$_{2f}$—(C$_3$–C$_8$)-cycloalkyl, quinolinyl, isoquinolinyl, pyridinyl, imidazolyl or phenyl, where the aromatic systems quinolinyl, isoquinolinyl, pyridinyl, imidazolyl and phenyl are unsubstituted or are substituted by 1–3 substituents chosen from the group consisting of F, Cl, CF$_3$, CH$_3$, methoxy, hydroxyl, amino, methylamino and dimethylamino;

f is zero or 1;

R(11) and R(12) are, independently of one another, defined as R(10), hydrogen or alkyl having 1, 2, 3 or 4 carbon atoms; and R(4) and R(5) are, independently of one another, hydrogen, alkyl having 1, 2 or 3 carbon atoms, F, Cl, OH, methoxy, NH$_2$ or —(CF$_2$)$_o$—CF$_3$;

o is zero or 1;

and pharmacologically acceptable salts thereof.

Especially preferred compounds of the formula I are those in which:

R(1) is CF$_3$—C(OH)$_2$—;

R(2) and R(3) are, independently of one another, hydrogen, F, Cl, alkyl having 1, 2, 3 or 4 carbon atoms, cycloalkyl having 3, 4, 5 or 6 carbon atoms, alkoxy having 1, 2, 3 or 4 carbon atoms or phenoxy, which is unsubstituted or is substituted by 1–3 substituents chosen from the group consisting of F, Cl, methyl and methoxy;

or

R(2) and R(3) are, independently of one another, —CR(7)=CR(8)R(9) or —C°CR(9);

R(7) is hydrogen or methyl;

R(8) and R(9) are, independently of one another, hydrogen, alkyl having 1, 2, 3 or 4 carbon atoms, cycloalkyl having 3, 4, 5, 6, 7 or 8 carbon atoms or phenyl, which is unsubstituted or is substituted by 1–3 substituents chosen from the group consisting of F, Cl, CF$_3$, methyl and methoxy;

or

R(2) and R(3) are, independently of one another, phenyl, C$_6$H$_5$—(C$_1$-C$_2$)-alkyl, naphthyl, biphenylyl, quinolinyl, isoquinolinyl or imidazolyl, where quinolinyl, isoquinolinyl or imidazolyl are bonded via C or N and where phenyl, C$_6$H$_5$—(C$_1$-C$_4$)-alkyl, naphthyl, biphenylyl, quinolinyl, isoquinolinyl and imidazolyl are unsubstituted or are substituted by 1–3 substituents chosen from the group consisting of F, Cl, CF$_3$, CH$_3$, methoxy, hydroxyl, amino, methylamino and dimethylamino;

or

R(2) and R(3) are, independently of one another, SR(10), —OR(10) or —CR(10)R(11)R(12);

R(10) is —C$_f$H$_{2f}$—(C$_3$-C8)-cycloalkyl, quinolinyl, isoquinolinyl, pyridinyl, imidazolyl or phenyl, where the aromatic systems quinolinyl, isoquinolinyl, pyridinyl, imidazolyl and phenyl are unsubstituted or are substituted by 1–3 substituents chosen from the group consisting of F, Cl, CF$_3$, CH$_3$, methoxy, hydroxyl, amino, methylamino and dimethylamino;

f is zero or 1

R(11) and R(12) are, independently of one another, defined as R(10), hydrogen or alkyl having 1, 2, 3 or 4 carbon atoms; and R(4) and R(5) are, independently of one another, hydrogen, alkyl having 1, 2 or 3 carbon atoms, F, Cl, OCH$_3$ or —CF$_3$;

and pharmacologically acceptable salts thereof.

The alkyl radicals mentioned can be in either straight-chain or branched form.

The invention furthermore relates to a process for the preparation of the compounds 1, which comprises reacting a compound of the formula II

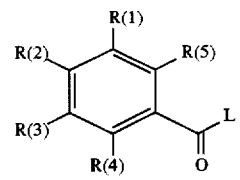

in which R(1) to R(5) have the meaning given and L is a leaving group which can easily be replaced nucleophilically, with guanidine and optionally comprises converting the product into a pharmacologically acceptable salt.

DETAILED DESCRIPTION OF THE INVENTION

The activated acid derivatives of the formula II in which L is an alkoxy, preferably a methoxy group, a phenoxy group, a phenylthio, methylthio or 2-pyridylthio group or a nitrogen-containing heterocyclic radical, preferably 1-imidazolyl, are advantageously obtained in a manner known per se from the carboxylic acid chlorides on which they are based (formula II, L=Cl), which in turn can be prepared again in a manner known per se from the carboxylic acids on which they are based (formula II, L=OH), for example with thionyl chloride.

In addition to the carboxylic acid chlorides of the formula II (L=Cl), other activated acid derivatives of the formula II can also be prepared in a manner known per se directly from the benzoic acid derivatives on which they are based (formula II, L=OH), such as, for example, the methyl esters of the formula II where L=OCH$_3$ can be prepared by treatment with gaseous HCl in methanol, the imidazolides of the formula II can be prepared by treatment with carbonyldiimidazole [L=1-imidazolyl, Staab, Angew. Chem. Int. Ed. Engl. 1, 351–367 (1962)], and the mixed anhydrides II can be prepared with Cl—COOC$_2$H$_5$ or tosyl chloride in the presence of triethylamine in an inert solvent. Benzoic acids can also be activated with dicyclohexylcarbodiimide (DCC) or with O—[(cyano(ethoxycarbonyl)methylene)amino]-1,1,3,3-tetramethyluronium tetrafluoroborate ("TOTU") [Weiss and Krommer, Chemiker Zeitung 98, 817 (1974)]. A number of suitable methods for the preparation of activated carboxylic acid derivatives of the formula 11 are mentioned with reference to source literature in J. March, Advanced Organic Chemistry, Third Edition (John Wiley & Sons, 1985), page 350.

The reaction of an activated carboxylic acid derivative of the formula II with guanidine is carried out in a manner known per se in a protic or aprotic polar but inert organic solvent. Methanol, isopropanol and tetrahydrofuran at from 20° C. up to the boiling point of these solvents have proven suitable for the reaction of the benzoic acid methyl esters (II, L=OMe) with guanidine. Most of the reactions of compounds II with salt-free guanidine were advantageously carried out in aprotic inert solvents, such as tetrahydrofuran, dimethoxyethane or dioxane. However, water can also be used as the solvent for the reaction of II with guanidine using a base, such as, for example, NaOH. If L=Cl, the reaction is advantageously carried out with addition of an acid-trapping agent, for example in the form of excess guanidine, to bond the hydrogen halide acid.

Some of the benzoic acid derivatives of the formula II on which the compounds are based are known and are described in the literature. The compounds of the formula II which are not known can be prepared by methods known from the literature. The resulting benzoic acid derivatives are first reacted with aqueous sodium hydroxide solution to give the corresponding bis-hydroxy compounds, and these are then reacted by one of the process variants described above to give compounds I according to the invention.

Some of the substituents are introduced by methods known from the literature for palladium-mediated cross-coupling of aryl halides or aryl triflates with, for example, organostannanes, organoboron acids or organoboranes or organocopper compounds or organozinc compounds.

Some substituents are introduced by methods known from the literature for nucleophilic substitution on an aromatic ring.

Benzoylguanidines I are in general weak bases and can bond acid to form salts. Possible acid addition salts are salts of all the pharmacologically tolerated acids, for example halides, in particular hydrochlorides, lactates, sulfates, citrates, tartrates, acetates, phosphates, methylsulfonates and p-toluenesulfonates.

The compounds I are substituted acylguanidines. The most prominent representative of the acylguanidines is the pyrazine derivative amiloride, which is used in treatment as a potassium-saving diuretic. Numerous other compounds of the amiloride type are described in the literature, such as, for example, dimethylamiloride or ethylisopropylamiloride.

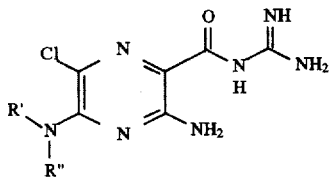

Amiloride: R',R"=H
Dimethylamiloride: R',R"=CH$_3$
Ethylisopropylamiloride: R'=C$_2$H$_5$, R"=CH(CH$_3$)$_2$ Studies which indicate antiarrhythmic properties of amiloride have furthermore been disclosed (Circulation 79, 1257–63 (1989)). Widespread use as an antiarrhythmic is opposed, however, by the fact that this effect is only weak and occurs accompanied by an antihypertensive and saluretic action, and that these side effects are undesirable in the treatment of disorders in cardiac rhythm.

Indications of antiarrhythmic properties of amiloride have also been obtained in experiments on isolated animal hearts (Eur. Heart J. 9 (supplement 1): 167 (1988) (book of abstracts)). It has thus been found, for example in rat hearts, that it was possible for artificially induced ventricular fibrillation to be suppressed completely by amiloride. The above mentioned amiloride derivative ethylisopropylamiloride was even more potent than amiloride in this model.

U.S. Pat. No. 5,091,394 (HOE 89/F 288) describes benzoylguanidines which carry a hydrogen atom in the position corresponding to the radical R(1). EP-A-0 556 674 (HOE 92/F 034) discloses benzoylguanidines in which, however, the substituents do not have the meanings claimed according to the present invention.

U.S. Pat. No. 3,780,027 claims acylguanidines which are structurally similar to the compounds of the formula I and are derived from commercially available loop diuretics, such as bumetanide. A potent salidiuretic activity is reported correspondingly for these compounds.

Compared with the known benzoylguanidines, for example from U.S. Pat. No. 5,091,394 (HOE 89/F 288) or EP-A 602 522 (HOE 92/F404), the compounds according to the invention are distinguished by the fact that the novel substituent R(6)—C(OH)$_2$— causes a very high water-solubility of the compounds 1 because of the geminal bis-hydroxy functionality.

It was surprising that the compounds according to the invention have no undesirable and adverse salidiuretic properties but have very good antiarrhythmic properties, such as are important, for example, for treatment of diseases which occur with oxygen deficiency symptoms. As a result of their pharmacological properties, the compounds are outstandingly suitable as antiarrhythmic medicaments with a cardioprotective component for prophylaxis of infarction and infarction treatment and for treatment of angina pectoris, where they also preventively inhibit or greatly reduce the pathophysiological processes in the development of ischemically induced damage, in particular in the triggering of ischemically induced cardiac arrhythmia's. Because of their protective actions against pathological hypoxic and ischemic situations, the compounds of the formula 1 according to the invention can be used, as a result of inhibition of the cellular Na$^+$/H$^+$ exchange mechanism, as medicaments for treatment of all acute or chronic damage caused by ischemia or diseases induced primarily or secondarily by this means. This applies to their use as medicaments for surgical operations, for example for organ transplants, where the compounds can be used both to protect the organs in the donor before and during removal, to protect removed organs, for example during treatment with, or storage thereof in, physiological bathing liquids, and during transfer into the recipient organism. The compounds are likewise valuable medicaments having a protective action for carrying out angioplastic surgical operations, for example on the heart and also on peripheral vessels. In accordance with their protective action against ischemically induced damage, the compounds are also suitable as medicaments for treatment of ischemia of the nervous system, in particular the central nervous system, where they are suitable, for example, for treatment of apoplexy or cerebral edema. The compounds of the formula I according to the invention furthermore are likewise suitable for treatment of forms of shock, for example of allergic, cardiogenic, hypovolemic and bacterial shock.

The compounds of the formula I according to the invention moreover are distinguished by a strong inhibiting action on the proliferation of cells, for example fibroblast cell proliferation and proliferation of smooth vascular muscle cells. The compounds of the formula I are therefore suitable as valuable therapeutics for diseases in which cell proliferation is a primary or secondary cause, and they can therefore be used as antiatherosclerotics, agents against delayed diabetic complications, cancer diseases, fibrotic diseases such as pulmonary fibrosis, hepatic fibrosis or renal fibrosis, and organ hypertrophies and hyperplasias, in particular in prostate hyperplasia or prostate hypertrophy.

The compounds according to the invention are effective inhibitors of the cellular sodium-proton antiporter (Na$^+$/H$^+$ exchanger), which is increased with numerous diseases (essential hypertension, atherosclerosis, diabetes and the like), including in those cells which are readily accessible for measurements, such as, for example, in erythrocytes, platelets or leukocytes. The compounds according to the invention are therefore suitable as outstanding and simple scientific tools, for example in their use as diagnostic agents for determination of and differentiation between certain forms of hypertension, and also atherosclerosis, diabetes, proliferative diseases and the like. The compounds of the formula I are furthermore suitable for preventive treatment to prevent the origin of high blood pressure, for example essential hypertension.

Medicaments which comprise a compound I can be administered here orally, parenterally, intravenously, rectally or by inhalation, the preferred administration depending on the particular clinical picture of the disease. The compounds I can be used here by themselves or together with pharmaceutical auxiliaries, both in veterinary medicine and in human medicine.

The expert is familiar with the auxiliaries which are suitable for the desired medicament formulation on the basis of his expert knowledge. In addition to solvents, gel-forming agents, suppository bases, tabletting auxiliaries and other active compound excipients, it is possible to use, for example, antioxidants, dispersing agents, emulsifiers, antifoams, flavor correctants, preservatives, solubilizing agents or dyestuffs.

For an oral use form, the active compounds are mixed with the additives suitable for this form, such as excipients, stabilizers or inert diluents, and the mixture is brought by the customary methods into the suitable dosage forms, such as tablets, coated tablets, hard gelatin capsules and aqueous, alcoholic or oily solutions. Inert excipients which can be used are, for example, gum arabic, magnesia, magnesium carbonate, potassium phosphate, lactates, glucose or starch, in particular maize starch. Formulation can be carried out here on the basis of either dry or moist granules. Possible oily excipients or solvents are, for example, vegetable or animal oils, such as sunflower oil or cod-liver oil.

For subcutaneous or intravenous administration, the active compounds are dissolved, suspended or emulsified, if desired with the substances customary for this, such as solubilizing agents, emulsifiers or other auxiliaries. Possible solvent are, for example: water, physiological saline solution or alcohols, for example ethanol, propanol or glycerol, and in addition also sugar solutions, such as glucose solutions or mannitol solutions, or also a mixture of the various solvents mentioned.

Suitable pharmaceutical formulations for administration in the form of aerosols or sprays are, for example, solutions, suspensions or emulsions of the active compound of the formula I in a pharmaceutically acceptable solvent, such as, in particular, ethanol or water, or a mixture of such solvents.

If required, the formulation can also additionally comprise other pharmaceutical auxiliaries, such as surfactants, emulsifiers and stabilizers, as well as a propellant gas. Such a formulation usually comprises the active compound in a concentration of about 0.1 to 10, in particular about 0.3 to 3, % by weight.

The dosage of the active compound of the formula I to be administered and the frequency of administration depend on the action strength and duration of action of the compounds used; furthermore also on the nature and severity of the disease to be treated and on the sex, age, weight and individual response of the mammal to be treated.

The daily dose of a compound of the formula I for a patient weighing about 75 kg is on average at least 0.001 mg/kg, preferably 0.01 mg/kg, to not more than 10 mg/kg, preferably 1 mg/kg, of body weight. For acute onsets of the disease, for example immediately after a cardiac infarction has been suffered, even higher and above all more frequent dosages may also be necessary, for example up to 4 individual doses per day. Up to 200 mg per day may be necessary for i.v. use in particular, for example for an infarction patient in intensive care.

List of abbreviations:

| | |
|---|---|
| MeOH | Methanol |
| DMF | N,N-Dimethylformamide |
| NBS | N-Bromosuccinimide |
| AIBN | a,a-Azo-bis-isobutyronitrile |
| EI | Electron impact |
| DCI | Desorption-Chemical Ionization |
| RT | Room temperature |
| EA | Ethyl acetate (EtOAc) |
| DIP | Diisopropyl ether |
| MTB | Methyl tert-butyl ether |
| mp | Melting point |
| HEP | n-Heptane |
| DME | Dimethoxyethane |
| FAB | Fast Atom Bombardment |
| $CH_2Cl_2$ | Dichloromethane |
| THF | Tetrahydrofuran |
| eq | Equivalent |
| ES | Electrospray ionization |

Experimental Part

General instructions for preparation of benzoylguanidines (I)

Variant A: from benzoic acids (II, L=OH)

0.01 mol of the benzoic acid derivative of formula II is dissolved or suspended in 60 ml of anhydrous THF, and 1.78 g (0.011 mol) of carbonyldiimidazole is then added. After stirring at RT for 2 hours, 2.95 g (0.05 mol) of guanidine is introduced into the reaction solution. After stirring overnight, the THF is distilled off under reduced pressure (Rotavapor), water is added, the pH is brought to 6 to 7 using 2N HCl and the corresponding benzoylguanidine (formula I) is filtered off. The benzoylguanidines thus obtained can be converted into the corresponding salts by treatment with aqueous, methanolic or ethereal hydrochloric acid or other pharmacologically tolerated acids.

General instructions for the preparation of benzoylguanidines (I)

Variant B: from benzoic acid alkyl esters (II, L=O-alkyl)

5 mmol of the benzoic acid alkyl ester of the formula II and 25 mmol of guanidine (free base) is dissolved in 15 ml of isopropanol or suspended in 15 ml of THF and the solution or suspension is boiled under reflux until conversion is complete (monitoring by thin layer chromatography; typical reaction time 2 to 5 hours). The solvent is distilled off under reduced pressure (Rotavapor), the residue is taken up in 300 ml of EA and the mixture is washed 3 times with 50 ml of $NaHCO_3$ solution each time. It is dried over $Na_2SO_4$, the solvent is distilled off in vacuo and the residue is chromatographed over silica gel using a suitable mobile phase, for example EA/MeOH 5:1.

(For salt formation, cf. variant A)

EXAMPLE 1

4-(1',1'-bishydroxy-2',2',2'-trifluoro)-ethyl-benzoylguanidine hydrochloride

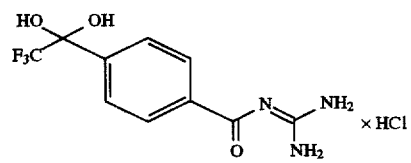

colorless crystals MS (ESI) M$^+$+H: 278

Synthesis route:

From 4-trifluoroacetylbenzoic acid according to general instructions, variant A.

EXAMPLE 2

4-fluoro-3-(1',1'-bishydroxy-2',2',2'-trifluoro)ethyl-benzoylguanidine hydrochloride.

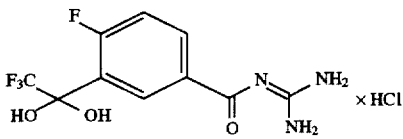

colorless crystals MS (ESI), M$^+$+H: 296
Synthesis route:

a) 4-Fluoro-3-trifluoroacetylbenzoic acid from 3-bromo-4-fluorobenzoic acid by metal-halogen exchange with n-butyllithium at −70° C. in THF followed by trifluoroacetylation using N-trifluoroacetylpiperidine, aqueous working up, colorless oil, M$^+$+H=255.

b) 4-Fluoro-3-trifluoroacetylbenzoyl chloride from a) by heating with thionyl chloride in toluene, brownish oil, M$^+$+H=273.

c) 4-Fluoro-3-(1',1'-bishydroxy-2',2',2'-trifluoro) ethylbenzoylguanidine hydrochloride by stirring with guanidine at RT in THF for 4 h followed by formation of the hydrochloride with hydrogen chloride in ether.

EXAMPLE 3

4-Isopropyl-3-(1',1'-bishydroxy-2',2', 2'-trifluoro) ethylbenzoylquanidine hydrochloride

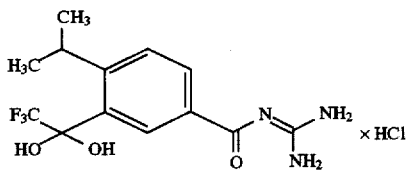

colorless crystals MS (ESI) M$^+$+H=320:
Synthesis route:

a) 3-Bromo-4-isopropylbenzoic acid from 3-amino-4-isopropylbenzoic acid by diazotization with sodium nitrite in glacial acetic acid at 0° C. followed by Sandmeyer reaction with copper(I) bromide in aqueous HBr at RT,
colorless crystals, mp 148° C.

b) 4-Isopropyl-3-trifluoroacetylbenzoic acid from a) by metal-halogen exchange with n-butyllithium at −70° C. in THF followed by trifluoroacetylation using N-trifluoroacetylpiperidine, aqueous working up,
colorless oil, M$^+$+H=261.

c) Methyl 4-isopropyl-3-trifluoroacetylbenzoate from b) by reaction with acetyl chloride in methanol at RT, aqueous working up, column chromatography with cyclohexane/ethyl acetate 9:5,
colorless oil, M$^+$+H=275.

d) 4-Isopropyl-3-(1',1'-bishydroxy-2',2',2'-trifluoro) ethylbenzoylguanidine hydrochloride from c) according to general instructions, method B.

Pharmacological data:
Inhibition of the Na$^+$/H$^+$ exchanger of rabbit erythrocytes White New Zealand rabbits (Ivanovas) received a standard diet containing 2% cholesterol for six weeks in order to activate the Na$^+$/H$^+$ exchange and thereby to enable determination of the Na$^+$ influx into the erythrocytes via Na$^+$/H$^+$ exchange using flame photometry. Blood was removed from the arteries of the ear and rendered noncoagulable by means of 25 IU of potassium-heparin. A portion of each sample was used for duplicate determination of the hematocrit by centrifugation. Aliquots each of 100 ml were used to measure the initial Na$^+$ content of the erythrocytes.

In order to determine the amiloride-sensitive sodium influx, 100 ml of each blood sample were in each case incubated, at a pH of 7.4 and at 37° C., in 5 ml of a hyperosmolar salt/sucrose medium (mmol/l: 140 NaCl, 3 KCl, 150 sucrose, 0.1 ouabain, 20 tris-hydroxymethylaminomethane). The erythrocytes were subsequently washed three times with ice-cold MgCl$_2$/ouabain solution (mmol/l: 112 MgCl$_2$, 0.1 ouabain) and hemolyzed in 2.0 ml of distilled water. The intracellular sodium content was determined by flame photometry.

The net influx of Na$^+$ was determined from the difference between initial sodium values and the sodium content of the erythrocytes following incubation. The sodium influx which can be inhibited by amiloride was given by the difference in the sodium content of the erythrocytes following incubation with and without 3·10$^{-4}$ mol/l amiloride. The same procedure was followed when using the compounds according to the invention.

| Inhibition of the Na$^+$/H$^+$ exchanger: | |
|---|---|
| Example | IC$_{50}$ (mmol/l) |
| 1 | 1.5 |
| 2 | 1.0 |
| 3 | 0.3 |

What is claimed is:
1. A benzoylguanidine of the formula I

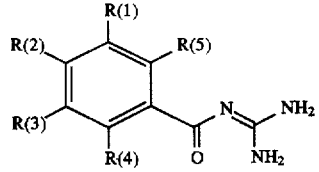

in which:
at least one of the substituents R(1), R(2) and R(3) is

R(6)—C(OH)$_2$—;

R(6) is perfluoroalkyl having 1, 2 or 3 carbon atoms, which is straight-chain or branched;

and the other substituents R(1), R(2) and R(3) are, independently of one another, hydrogen, OH, F, Cl, Br, I, alkyl having 1, 2, 3, 4, 5 or 6 carbon atoms, cycloalkyl having 3, 4, 5 or 6 carbon atoms, alkoxy having 1, 2, 3 or 4 carbon atoms or phenoxy, which is unsubstituted or is substituted by 1–3 substituents chosen from the group consisting of F, Cl, methyl and methoxy;

or the other substituents R(1), R(2) and R(3) are, independently of one another, alkyl-SO$_x$, —CR(7)=CR(8)R (9) or —C°CR(9);

x is zero, 1 or 2;

R(7) is hydrogen or methyl;

R(8) and R(9) are, independently of one another, hydrogen, alkyl having 1, 2, 3 or 4 carbon atoms, cycloalkyl having 3, 4, 5, 6, 7 or 8 carbon atoms or phenyl, which is unsubstituted or is substituted by 1–3 substituents chosen from the group consisting of F, Cl, CF$_3$, methyl and methoxy;

or the other substituents R(1), R(2) and R(3) are, independently of one another, phenyl, C$_6$H$_5$—(C$_1$-C$_4$)-alkyl, naphthyl, biphenylyl, quinolinyl, isoquinolinyl or imidazolyl, where quinolinyl, isoquinolinyl or imidazolyl are bonded via C or N and where phenyl, C$_6$H$_5$—(C$_1$-C$_4$)-alkyl, naphthyl, biphenylyl, quinolinyl, isoquinolinyl and imidazolyl are unsubstituted or are substituted by 1–3 substituents chosen from the group consisting of F, Cl, CF$_3$, CH$_3$, methoxy, hydroxyl, amino, methylamino and dimethylamino;

or the other substituents R(1), R(2) and R(3) are, independently of one another, SR(10), —OR(10) or —CR(10)R(11)R(12);

R(10) is —C$_f$H$_{2f}$—(C$_3$-C$_8$)-cycloalkyl, quinolinyl, isoquinolinyl, pyridinyl, imidazolyl or phenyl, where the aromatic systems quinolinyl, isoquinolinyl, pyridinyl, imidazolyl and phenyl are unsubstituted or are substituted by 1–3 substituents chosen from the group consisting of F, Cl, CF$_3$, CH$_3$, methoxy, hydroxyl, amino, methylamino and dimethylamino;

f is zero, 1 or 2;

R(11) and R(12) are, independently of one another, defined as R(10), hydrogen or alkyl having 1, 2, 3 or 4 carbon atoms; and R(4) and R(5) are, independently of one another, hydrogen, alkyl having 1, 2 or 3 carbon atoms, F, Cl, Br, I, CN, OR(13), NR(14)R(15) or —(CH$_2$)$_n$—(CF$_2$)$_o$—CF$_3$;

R(13), R(14) and R(15) are, independently of one another, hydrogen or alkyl having 1, 2, 3 or 4 carbon atoms;

n is zero or 1;

o is zero, 1 or 2;

or a pharmacologically acceptable salt thereof.

2. A compound according to claim 1, wherein at least one of the substituents R(1), R(2) and R(3) is CF$_3$—C(OH)$_2$—;

and the other substituents R(1), R(2) and R(3) are, independently of one another, hydrogen, F, Cl, alkyl having 1, 2, 3, 4, 5 or 6 carbon atoms, cycloalkyl having 3, 4, 5 or 6 carbon atoms, alkoxy having 1, 2, 3 or 4 carbon atoms or phenoxy, which is unsubstituted or is substituted by 1–3 substituents chosen from the group consisting of F, Cl, methyl and methoxy;

or the other substituents R(1), R(2) and R(3) are, independently of one another, alkyl-SO$_x$, —CR(7)=CR(8)R(9) or —C°CR(9);

x is zero, 1 or 2;

R(7) is hydrogen or methyl;

R(8) and R(9) are, independently of one another, hydrogen, alkyl having 1, 2, 3 or 4 carbon atoms, cycloalkyl having 3, 4, 5, 6, 7 or 8 carbon atoms or phenyl, which is unsubstituted or is substituted by 1–3 substituents chosen from the group consisting of F, Cl, CF$_3$, methyl and methoxy;

or the other substituents R(1), R(2) and R(3) are, independently of one another, phenyl, C$_6$H$_5$—(C$_1$-C$_2$)-alkyl, naphthyl, biphenylyl, quinolinyl, isoquinolinyl or imidazolyl, where quinolinyl, isoquinolinyl or imidazolyl are bonded via C or N and where phenyl, C$_6$H$_5$—(C$_1$-C$_4$)-alkyl, naphthyl, biphenylyl, quinolinyl, isoquinolinyl and imidazolyl are unsubstituted or are substituted by 1–3 substituents chosen from the group consisting of F, Cl, CF$_3$, CH$_3$, methoxy, hydroxyl, amino, methylamino and dimethylamino;

or the other substituents R(1), R(2) and R(3) are, independently of one another, SR(10), —OR(10) or —CR(10)R(11)R(12);

R(10) is —C$_f$H$_{2f}$—(C$_3$-C$_8$)-cycloalkyl, quinolinyl, isoquinolinyl, pyridinyl, imidazolyl or phenyl, where the aromatic systems quinolinyl, isoquinolinyl, pyridinyl, imidazolyl and phenyl are unsubstituted or are substituted by 1–3 substituents chosen from the group consisting of F, Cl, CF$_3$, CH$_3$, methoxy, hydroxyl, amino, methylamino and dimethylamino;

f is zero or 1;

R(11) and R(12) are, independently of one another, defined as R(10), hydrogen or alkyl having 1, 2, 3 or 4 carbon atoms; and R(4) and R(5) are, independently of one another, hydrogen, alkyl having 1, 2 or 3 carbon atoms, F, Cl, OH, methoxy, NH$_2$ or —(CF$_2$)$_o$—CF$_3$;

o is zero or 1.

3. A compound according to claim 1 wherein;

R(1) is CF$_3$—C(OH)$_2$—;

R(2) and R(3) are, independently of one another, hydrogen, F, Cl, alkyl having 1, 2, 3 or 4 carbon atoms, cycloalkyl having 3, 4, 5 or 6 carbon atoms, alkoxy having 1, 2, 3 or 4 carbon atoms or phenoxy, which is unsubstituted or is substituted by 1–3 substituents chosen from the group consisting of F, Cl, methyl and methoxy;

or

R(2) and R(3) are, independently of one another, —CR(7)=CR(8)R(9) or —C°CR(9);

R(7) is hydrogen or methyl;

R(8) and R(9) are, independently of one another, hydrogen, alkyl having 1, 2, 3 or 4 carbon atoms, cycloalkyl having 3, 4, 5, 6, 7 or 8 carbon atoms or phenyl, which is unsubstituted or is substituted by 1–3 substituents chosen from the group consisting of F, Cl, CF$_3$, methyl and methoxy;

or

R(2) and R(3) are, independently of one another, phenyl, C$_6$H$_5$—(C$_1$-C$_2$)-alkyl, naphthyl, biphenylyl, quinolinyl, isoquinolinyl or imidazolyl, where quinolinyl, isoquinolinyl or imidazolyl are bonded via C or N and where phenyl, C$_6$H$_5$—(C$_1$-C$_4$)-alkyl, naphthyl, biphenylyl, quinolinyl, isoquinolinyl and imidazolyl are unsubstituted or are substituted by 1–3 substituents chosen from the group consisting of F, Cl, CF$_3$, CH$_3$, methoxy, hydroxyl, amino, methylamino and dimethylamino;

or

R(2) and R(3) are, independently of one another, SR(10), —OR(10) or —CR(10)R(11)R(12);

R(10) is —C$_f$H$_{2f}$—(C$_3$-C8)-cycloalkyl, quinolinyl, isoquinolinyl, pyridinyl, imidazolyl or phenyl, where the aromatic systems quinolinyl, isoquinolinyl, pyridinyl, imidazolyl and phenyl are unsubstituted or are substituted by 1–3 substituents chosen from the group consisting of F, Cl, CF$_3$, CH$_3$, methoxy, hydroxyl, amino, methylamino and dimethylamino;

f is zero or 1;

R(11) and R(12) are, independently of one another, defined as R(10), hydrogen or alkyl having 1, 2, 3 or 4 carbon atoms; and R(4) and R(5) are, independently of one another, hydrogen, alkyl having 1, 2 or 3 carbon atoms, F, Cl, $OCH_3$ or $-CF_3$;

or a pharmacologically acceptable salt thereof.

4. A compound according to claim 1 wherein the compound is 4-(1',1'-bishydroxy-2',2',2'-trifluoro)-ethyl-benzoylguanidine hydrochloride.

5. A compound according to claim 1 wherein the compound is 4-fluoro-3-(1',1'-bishydroxy-2',2',2'-trifluoro)ethyl-benzoylguanidine hydrochloride.

6. A compound according to claim 1 wherein the compound is 4-Isopropyl-3-(1',1'-bishydroxy-2',2',2'-trifluoro) ethylbenzoylguanidine hydrochloride.

7. A process for the preparation of a compound I according to claim 1, which comprises reacting a compound of the formula II

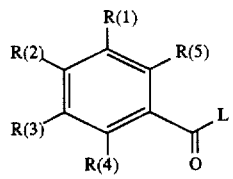

in which R(1) to R(5) have the meaning given and L is a leaving group which can easily be replaced nucleophilically, with guanidine.

8. A method of treating arrhythmias comprising administering to a subject in need thereof an effective amount of a compound according to either claim 1, claim 2, or claim 3.

9. A method of treating cardiac infarction comprising administering to a subject in need thereof an effective amount of a compound according to either claim 1, claim 2, or claim 3.

10. A method of treating angina pectoris comprising administering to a subject in need thereof an effective amount of a compound according to either claim 1, claim 2 or claim 3.

11. A method of treating ischemic states of the heart comprising administering to a subject in need thereof an effective amount of a compound according to either claim 1, claim 2 or claim 3.

12. A method of treating ischemic states of the peripheral and central nervous system and of apoplexy comprising administering to a subject in need thereof an effective amount of a compound according to either claim 1, claim 2, or claim 3.

13. A method of treating ischemic states of peripheral organs and limbs comprising administering to a subject in need thereof an effective amount of a compound according to either claim 1, claim 2, or claim 3.

14. A method of treating shock states comprising administering to a subject in need thereof an effective amount of a compound according to either claim 1, claim 2, or claim 3.

15. A method of protecting subjects or organs during surgical operations or organ transplants comprising administering an effective amount of a compound according to either claim 1, claim 2 or claim 3.

16. A method of preserving or storing transplants for surgical measures comprising administering an effective amount of a compound according to either claim 1, claim 2 or claim 3.

17. A method of treating diseases in which cell proliferation is a primary or secondary cause comprising administering to a subject in need thereof an effective amount of a compound according to either claim 1, claim 2, or claim 3.

18. A method according to claim 17 in which the diseases are atherosclerosis, delayed diabetic complications, cancer diseases, fibrotic diseases, or prostate hyperplasia.

19. method according to claim 18 in which the fibrotic diseases are pulmonary fibrosis, hepatic fibrosis, or renal fibrosis.

20. A method of inhibiting as a scientific tool the $Na^+/H^+$ exchanger and diagnosing hypertension and proliferative diseases, comprising using an effective amount of a compound according to either claim 1, claim 2, or claim 3.

21. A medicinal composition comprising an active amount of a compound according to either claim 1, claim 2, or claim 3.

* * * * *